(12) United States Patent
Hohmann

(10) Patent No.: US 7,748,282 B1
(45) Date of Patent: Jul. 6, 2010

(54) AVIATION FUEL SAMPLER DEVICE AND METHOD

(76) Inventor: Paul Hohmann, 100 N. Plainview Dr., Greenville, SC (US) 29611

( * ) Notice: Subject to any disclaimer, the term of this patent is extended or adjusted under 35 U.S.C. 154(b) by 466 days.

(21) Appl. No.: 11/800,219

(22) Filed: May 5, 2007

(51) Int. Cl.
*G01N 1/18* (2006.01)
(52) U.S. Cl. .................. 73/864.63; 73/864.51
(58) Field of Classification Search ......... 73/863.52, 73/863.57, 864.51, 864.63
See application file for complete search history.

(56) References Cited

U.S. PATENT DOCUMENTS

| | | | | |
|---|---|---|---|---|
| 3,198,016 | A | * | 8/1965 | Poorman ............... 73/863.86 |
| 3,976,572 | A | | 8/1976 | Reick |
| 4,289,027 | A | * | 9/1981 | Gleaves et al. ........... 73/863.86 |
| 4,453,579 | A | * | 6/1984 | Gould ................... 141/329 |
| 4,700,580 | A | | 10/1987 | Kamin |
| 6,360,619 | B1 | * | 3/2002 | Schultz, Jr. ............. 73/863.86 |
| 7,377,151 | B1 | * | 5/2008 | Magee .................. 73/61.61 |
| 7,491,328 | B2 | * | 2/2009 | Brodbeck et al. ........... 210/232 |

* cited by examiner

*Primary Examiner*—Hezron Williams
*Assistant Examiner*—Nashmiya S Fayyaz
(74) *Attorney, Agent, or Firm*—Robert Nathans; Nathans Withsatend

(57) ABSTRACT

An aircraft fuel contaminant tester has an upper transparent chamber for viewing a first sample of aviation fuel, a lower chamber, a fuel cell drain valve actuating device for loading the upper transparent chamber. A thumb actuated valve halts flow of fuel from the upper chamber into the lower chamber until actuated by the pilot after viewing contaminated fuel in the upper transparent chamber. The larger lower chamber permits several samples of fuel to be repeatedly drained from the fuel tank and examined merely by manually actuating the valve without the undesired discarding of any fuel. When the fuel in the last batch of sampled fuel, viewed in the upper chamber, is free of contaminants, the inspection process ends and the tester is inverted, draining the sampled fuel from both chambers, usually at one time only, to eliminate the repeated discarding of the fuel from the commonly used sampler cup.

20 Claims, 1 Drawing Sheet

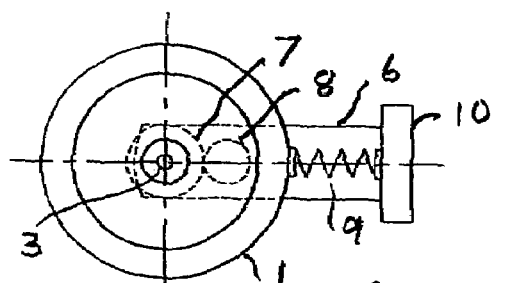
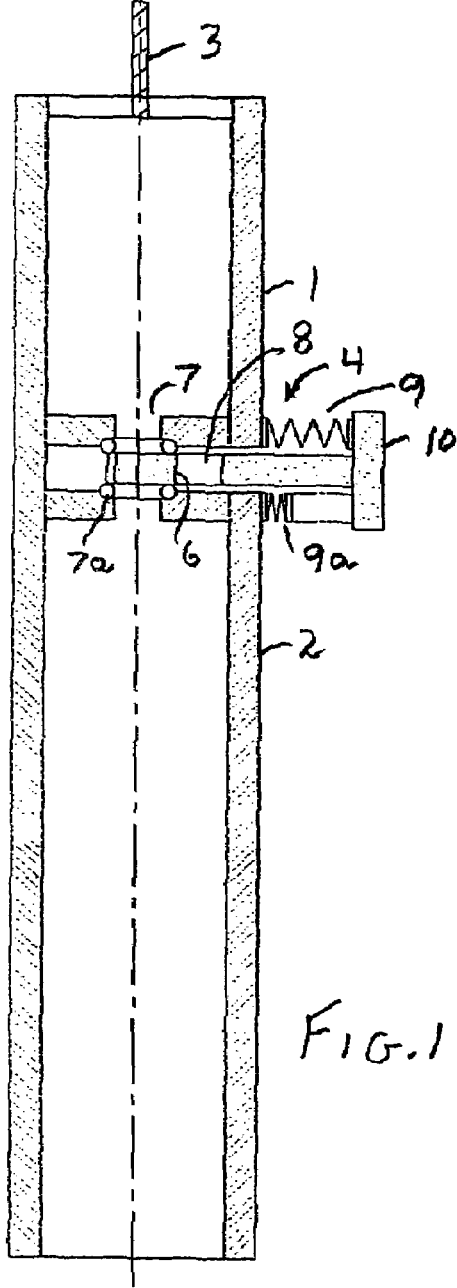

AVIATION FUEL SAMPLER DEVICE AND METHOD

BACKGROUND OF THE INVENTION

The invention relates to the field of aviation.

Part of the pre-flight check of aircraft is to visually inspect the fuel in the fuel cells to ensure that there is no foreign material in the gas tank that could possibly interrupt the flow of fuel from the tank into the engine(s). The primary foreign materials that can be found in the fuel are rust, scale and water; with water being the most common material that could interrupt the flow of fuel from the fuel tank into the engine. Since all of these materials are heavier than aviation fuel, they settle to the lowest part of the fuel tank which is called a sump. At the very bottom of the fuel tank sump is a drain valve.

A typical fuel test to detect contamination of fuel is accomplished by holding a standard fuel sampler cup under the fuel drain valve and allowing a small quantity of fuel, usually a few ounces, to drain into the standard cup. If there is no water or sediment in the sample, all of the fuel in the tank is considered clean and is either returned into the aircraft's fuel tank through the fuel fill valve, or more commonly, dumped on the ground. If however, there is a contaminant in the fuel sample, additional samples need to be taken.

With a standard fuel sampler cup there is only one chamber to drain the fuel into. Therefore all subsequent samples need to be taken into an empty sample cup to ensure that the previous retrieved impurity is gone and the fuel in the tank is actually clean. As a result, the repeatedly retrieved contaminated samples cannot be emptied back into the fuel tank so that they are normally discarded unto the ground until a clean sample is attained and the tank is considered to be free of impurities. This proves to be an ecological hazard and if witnessed, is punishable by a fine from the EPA. The current alternative in this situation is to empty the contaminated fuel samples into a waste fuel can until a clean sample can be attained. This proves to be tedious and time consuming; so not often practiced.

Also due to the geometry and configuration of the fuel tanks, many tanks have more than one fuel drain valve, some having as many as five or more per tank. With a standard sampler cup, the options are either to take a very small sample per drain valve, which is inadequate to truly sample the fuel in the tank, or repeatedly dump the fuel sample, back into the tank or on the ground, during each fuel test. This is again very tedious and time consuming.

It is thus desirable to provide a greatly improved fuel sampling device and fuel sampling method which will become effortless.

BRIEF SUMMARY OF A PREFERRED EMBODIMENT OF THE INVENTION

The objectives set forth above are met in accordance with the present invention, whereby an aircraft fuel contaminant tester is provided having an upper transparent cylindrical chamber suitable for storing and viewing aviation fuel by the pilot or other airport personnel, a lower cylindrical chamber several times larger than the upper chamber, a fuel cell drain valve actuating device coupled to the upper chamber, for enabling a sample of fuel from an aircraft fuel cell to pass into the upper transparent chamber for viewing by the pilot.

A thumb actuated valve halts flow of fuel from the upper chamber into the lower chamber until actuated by airport personnel after viewing the fuel in the upper transparent chamber. The lower chamber is at least several times larger than the upper chamber for permitting at least several samples of the aviation fuel to be repeatedly drained from the fuel cell or tank and visually examined, merely by manually actuating the valve without the aforesaid undesirable discarding of any fuel.

When the fuel in the last batch of sampled fuel, viewed in the upper chamber, is free of contaminants, the inspection process ends and the tester is inverted and the valve actuated, to drain the sampled fuel from both chambers, usually once, to eliminate the repeated discarding of the fuel from the commonly used sampler cup.

BRIEF DESCRIPTION OF THE DRAWINGS

FIG. 1 is a front sectional view of the preferred embodiment of the tester; and

FIG. 2 is a top view of the tester.

DESCRIPTION OF A CURRENTLY PREFERRED EMBODIMENT OF THE INVENTION

In FIG. 1 an upper transparent clear plastic cylindrical chamber 1 is coupled to a lower clear cylindrical plastic chamber 2. A conventional valve actuating pin 3 is affixed to the top of the upper chamber as shown and is adapted to engage the sump drain valve at the bottom of the aircraft's fuel tank in the conventional manner to cause a batch of fuel to fill the upper chamber. Valve 4 has a gate member 6 that prevents the fuel from falling into the lower chamber 2 at this time. If the pilot or other tester sees contaminants in the fuel, he or she manually actuates the valve 4 by pressing against valve button 10 with her thumb, causing orifice 8 in the flat gate member 6, best shown in the top view of FIG. 2, to be positioned over orifice 7, to in turn cause gravity to transfer the first sampled batch of fuel to the far larger, lower chamber 2. The tester then removes her thumb from the valve button 10 and spring member 9 causes the spring biased valve gate member 6 to return to the original position shown in FIGS. 1 and 2 to again block transfer of fuel from the upper chamber to the lower chamber. At 9a in FIG. 1, the spring is shown when compressed. A pair of O-rings or the like seals 7a are also shown.

A second sample is now taken to determine whether further contaminants are present. If contaminants are present in the second sample, the valve is again manually actuated to cause the sample to be sent to the lower chamber. This process is repeated until a clear sample is produced in the upper chamber. The testing device is then inverted while the valve is thumb actuated in order to eject the entire accumulated samples into a waste receptacle, generally at one time only. This eliminates the aforesaid undesirable process of having to repeatedly discard each small sample of contaminated fuel into a waste can, or commonly on the ground, producing an environmental hazard. The lower chamber is substantially larger than the upper chamber, so that several samples may be taken without emptying the testing device.

Thus an aircraft fuel contaminant testing method of the invention includes the steps of providing a two compartment device having a manually operated valve separating the compartments; draining a sample of aircraft fuel into the upper chamber; visually determining whether contaminants are present in fuel observed within the upper chamber; upon the determination of the presence of contaminants, manually actuating the valve for transferring fuel from the upper chamber into the lower chamber; and repeating the procedure until contaminants are no longer observed in fuel within the upper chamber.

While the invention has been described in connection with preferred embodiments, the description is not intended to limit the scope of the invention to the particular forms set forth, but on the contrary, it is intended to cover such alternatives, modifications, and equivalents as may be included within the spirit and scope of the invention as indicated by the language of the appended claims.

I claim:

1. An aircraft fuel contaminant tester comprising:
   (a) an upper chamber suitable for storing and enabling viewing of aviation fuel by aviation associated personnel;
   (b) a lower chamber, substantially larger than said upper chamber, suitable for storing aviation fuel;
   (c) a fuel cell drain valve actuating device coupled to said upper chamber for enabling a sample of fuel from an aircraft fuel tank to pass into said upper chamber for viewing by said aviation associated personnel; and
   (d) valve means for completely halting flow of fuel from said upper chamber to said lower chamber until actuated by aviation associated personnel after viewing the fuel in said upper chamber and for selectively permitting disposal of the fuel in the lower chamber upon inversion of the tester.

2. The tester of claim 1 wherein said upper chamber is at least partially transparent.

3. The tester of claim 1 wherein said valve means is manually operated.

4. The tester of claim 2 wherein said valve means is manually operated.

5. The tester of claim 1 wherein the lower chamber is at least several times larger than the upper chamber for permitting at least several samples of the aviation fuel to be repeatedly drained from the fuel tank and examined merely by actuating said valve means without discarding any fuel.

6. The tester of claim 2 wherein the lower chamber is at least several times larger than the upper chamber for permitting at least several samples of the aviation fuel to be repeatedly drained from the fuel tank and examined merely by actuating said valve means without discarding any fuel.

7. The tester of claim 3 wherein the lower chamber is at least several times larger than the upper chamber for permitting at least several samples of the aviation fuel to be repeatedly drained from the fuel tank and examined merely by actuating said valve means without discarding any fuel.

8. The tester of claim 4 wherein the lower chamber is at least several times larger than the upper chamber for permitting at least several samples of the aviation fuel to be repeatedly drained from the fuel tank and examined merely by actuating said valve means without discarding any fuel.

9. An aircraft fuel contaminant tester comprising:
   (a) an upper transparent chamber suitable for storing and viewing aviation fuel by aviation associated personnel;
   (b) a lower chamber suitable for storing aviation fuel;
   (c) a fuel cell drain valve actuating device coupled to said upper chamber for enabling a sample of fuel from an aircraft fuel tank to pass into said upper chamber for viewing by said aviation associated personnel;
   (d) manually operated valve means for completely halting flow of fuel from said upper chamber to said lower chamber until actuated by aviation associated personnel after viewing the fuel in said upper transparent chamber and for selectively permitting disposal of the fuel in the lower chamber upon inversion of the tester; and
   (e) wherein the lower chamber is at least several times larger than the upper chamber for permitting at least several samples of the aviation fuel to be repeatedly drained from the fuel tank and examined merely by actuating said valve means without discarding any fuel.

10. The tester of claim 9 wherein said manually operated valve means is a thumb actuated valve means.

11. The tester of claim 10 wherein said thumb actuated valve means remains open as long as manual pressure is applied thereto and closes upon release of the manual pressure.

12. The tester of claim 11 wherein said thumb actuated valve means has a gate member spring biased to isolate the upper chamber from the lower chamber.

13. The tester of claim 9 wherein said upper and lower chambers are clear transparent plastic cylinders and said fuel cell drain valve actuating device is a simple pin.

14. The tester of claim 10 wherein said upper and lower chambers are clear transparent plastic cylinders and said fuel cell drain valve actuating device is a simple pin.

15. The tester of claim 11 wherein said upper and lower chambers are clear transparent plastic cylinders and said fuel cell drain valve actuating device is a simple pin.

16. The tester of claim 12 wherein said upper and lower chambers are clear transparent plastic cylinders and said fuel cell drain valve actuating device is a simple pin.

17. An aircraft fuel contaminant testing method comprising the steps of
   (a) providing an aircraft fuel contaminant tester having an upper chamber suitable for storing and enabling viewing of a sample of aviation fuel by aviation associated personnel;
   (a-1) a lower chamber, substantially larger than said upper chamber, suitable for storing aviation fuel;
   (a-2) a fuel cell drain valve actuating device coupled to said upper chamber for enabling a sample of fuel from an aircraft fuel tank to pass into said upper chamber for viewing by said aviation associated personnel; and
   (a-3) valve means for completely halting flow of fuel from said upper chamber to said lower chamber until actuated by aviation associated personnel after viewing the fuel in said upper chamber and for selectively permitting disposal of the fuel in the lower chamber upon inversion of the tester;
   (b) draining a sample of aircraft fuel into the upper chamber;
   (c) visually determining whether contaminants are present in fuel observed within the upper chamber;
   (d) upon the determination of the presence of contaminants, actuating said valve means for transferring fuel from said upper chamber into said lower chamber; and
   (e) repeating steps (b), (c) and (d) until contaminants are no longer detected in a sample of fuel within said upper chamber.

18. The method of claim 17 including manually actuating said valve means in accordance with step (d) by pressing against the valve means with a thumb of a person performing the testing method.

19. The method of claim 17 including the steps of actuating said valve means while inverting the tester upon the detection of contaminant free fuel in said upper chamber.

20. The method of claim 18 including the steps of actuating said valve means while inverting the tester upon the detection of contaminant free fuel in said upper chamber.

* * * * *